US010292955B2

(12) United States Patent
Lee et al.

(10) Patent No.: US 10,292,955 B2
(45) Date of Patent: May 21, 2019

(54) COMPOSITION FOR EXTERNAL USE PREPARATION WITH IMPROVED TRANSDERMAL PERMEABILITY

(71) Applicant: HYUNDAI PHARM CO., LTD., Chungcheongnam-do (KR)

(72) Inventors: Dong il Lee, Gyeonggi-do (KR); Min ji Yoon, Seoul (KR); Pung Sok Lee, Gyeonggi-do (KR)

(73) Assignee: HYUNDAI PHARM CO., LTD., Cheonan-si, Chungcheongnam-do (KR)

( * ) Notice: Subject to any disclaimer, the term of this patent is extended or adjusted under 35 U.S.C. 154(b) by 0 days.

(21) Appl. No.: 14/779,927

(22) PCT Filed: Mar. 28, 2014

(86) PCT No.: PCT/KR2014/002676
§ 371 (c)(1),
(2) Date: Sep. 24, 2015

(87) PCT Pub. No.: WO2014/163338
PCT Pub. Date: Oct. 9, 2014

(65) Prior Publication Data
US 2016/0058723 A1 Mar. 3, 2016

(30) Foreign Application Priority Data

Apr. 4, 2013 (KR) .................. 10-2013-0036912
Mar. 28, 2014 (KR) .................. 10-2014-0036904

(51) Int. Cl.

| | | |
|---|---|---|
| *A61K 31/195* | (2006.01) | |
| *A61K 9/00* | (2006.01) | |
| *A61Q 19/02* | (2006.01) | |
| *A61K 47/08* | (2006.01) | |
| *A61K 47/10* | (2017.01) | |
| *A61K 47/14* | (2017.01) | |
| *A61K 47/26* | (2006.01) | |
| *A61K 9/06* | (2006.01) | |
| *A61K 8/44* | (2006.01) | |
| *A61Q 19/00* | (2006.01) | |

(52) U.S. Cl.
CPC .............. *A61K 31/195* (2013.01); *A61K 8/44* (2013.01); *A61K 9/0014* (2013.01); *A61K 9/06* (2013.01); *A61K 47/08* (2013.01); *A61K 47/10* (2013.01); *A61K 47/14* (2013.01); *A61K 47/26* (2013.01); *A61Q 19/00* (2013.01); *A61Q 19/02* (2013.01)

(58) Field of Classification Search
CPC .......... A61K 8/44; A61K 9/0014; A61K 9/06; A61K 19/02; A61K 31/195; A61K 47/08; A61K 47/10; A61K 47/14; A61K 47/26; A61Q 19/00
See application file for complete search history.

(56) References Cited

U.S. PATENT DOCUMENTS

| | | | | |
|---|---|---|---|---|
| 5,476,650 A | * | 12/1995 | Patel .................. | A61K 8/19 132/204 |
| 5,916,587 A | | 6/1999 | Min et al. | |
| 5,968,899 A | | 10/1999 | Sekine et al. | |
| 9,205,060 B2 | | 12/2015 | Kamakura et al. | |
| 2006/0142382 A1 | * | 6/2006 | Morimoto ............ | A61K 31/195 514/474 |
| 2008/0207570 A1 | * | 8/2008 | Segura-Orsoni | |
| 2009/0181075 A1 | | 7/2009 | Gordon et al. | |

FOREIGN PATENT DOCUMENTS

| | | | |
|---|---|---|---|
| CN | 101390820 | | 3/2009 |
| CN | 102065900 | | 5/2011 |
| CN | 102186454 | | 9/2011 |
| CN | 102481244 | | 5/2012 |
| EP | 0 685 229 A1 | | 12/1995 |
| JP | 1989-93519 | | 4/1989 |
| JP | 1991-279313 | | 12/1991 |
| JP | 07-206624 A | | 8/1995 |
| JP | 1996-500365 | | 1/1996 |
| JP | 08-325135 | | 12/1996 |
| JP | 2002-003358 | | 1/2002 |
| JP | 2002-003373 | | 1/2002 |
| JP | 2002-201122 | | 7/2002 |
| JP | 2003-160465 A | | 6/2003 |
| JP | 2005-068076 | | 3/2005 |
| JP | 2005-225837 | | 8/2005 |
| JP | 2005-225837 A | * | 8/2005 |
| JP | 2005-298370 | | 10/2005 |
| JP | 2005272454 A | * | 10/2005 |
| JP | 2006008630 A | * | 1/2006 |
| JP | 2006-206575 | | 8/2006 |
| JP | 2006-213696 | | 8/2006 |
| JP | 2006-312603 | | 11/2006 |
| JP | 2007-291130 | | 11/2007 |
| JP | 2008-100933 | | 5/2008 |

(Continued)

OTHER PUBLICATIONS

International Search Report mailed in International Patent Application No. PCT/KR2014/002676 dated (Jul. 22, 2014).
Search Report from the State Intellectual Property Office of China for Application No. 201480018396.0 dated Oct. 11, 2016 (2 pages, which includes an English abstract on first page).
Cosmeticstage vol. 4, No. 7 (2010) & its English translation of the related parts.
Dictionary of Cosmetic components 2001, p. 62~63, Oct. 1, 2000 & its English translation of the related parts.
Japan Food Research Laboratories, vol. 3, No. 16, Apr. 2010 & its English translation of the related parts.

*Primary Examiner* — Ali Soroush
(74) *Attorney, Agent, or Firm* — Lex IP Meister, PLLC

(57) ABSTRACT

Provided is a skin external composition, which includes tranexamic acid or a salt thereof and a skin penetration enhancer, thereby showing remarkably increased skin permeability and improved sense of use, skin irritation, and storage stability.

10 Claims, 3 Drawing Sheets

(56) References Cited

FOREIGN PATENT DOCUMENTS

| | | | |
|---|---|---|---|
| JP | 2009-501722 | | 1/2009 |
| JP | 2010116392 | A | 5/2010 |
| JP | 2010202565 | A | 9/2010 |
| JP | 2010-229100 | | 10/2010 |
| JP | 2010-229100 | A | 10/2010 |
| JP | 2010229100 | A * | 10/2010 |
| JP | 2011016786 | A | 1/2011 |
| JP | 2011-068598 | | 4/2011 |
| JP | 2011084551 | A | 4/2011 |
| JP | 2011-173819 | | 9/2011 |
| JP | 2012-184270 | | 9/2012 |
| JP | 2013-014633 | | 1/2013 |
| KR | 10-0418489 | B1 | 2/2004 |
| KR | 10-2010-0103830 | A | 9/2010 |
| KR | 10-2011-0046585 | A | 5/2011 |
| KR | 10-1087602 | B1 | 11/2011 |
| KR | 10-2012-0004556 | A | 1/2012 |
| KR | 10-1159574 | B1 | 6/2012 |
| WO | 2004-060364 | | 7/2004 |
| WO | 2005-041967 | | 5/2005 |
| WO | 2007-077741 | | 7/2007 |
| WO | 2011-132966 | | 10/2011 |
| WO | WO-2011122840 | A2 * | 10/2011 ............... A61K 8/44 |
| WO | 2013-005760 | | 1/2013 |
| WO | 2014/163338 | A1 | 9/2014 |

* cited by examiner

[FIG. 1]
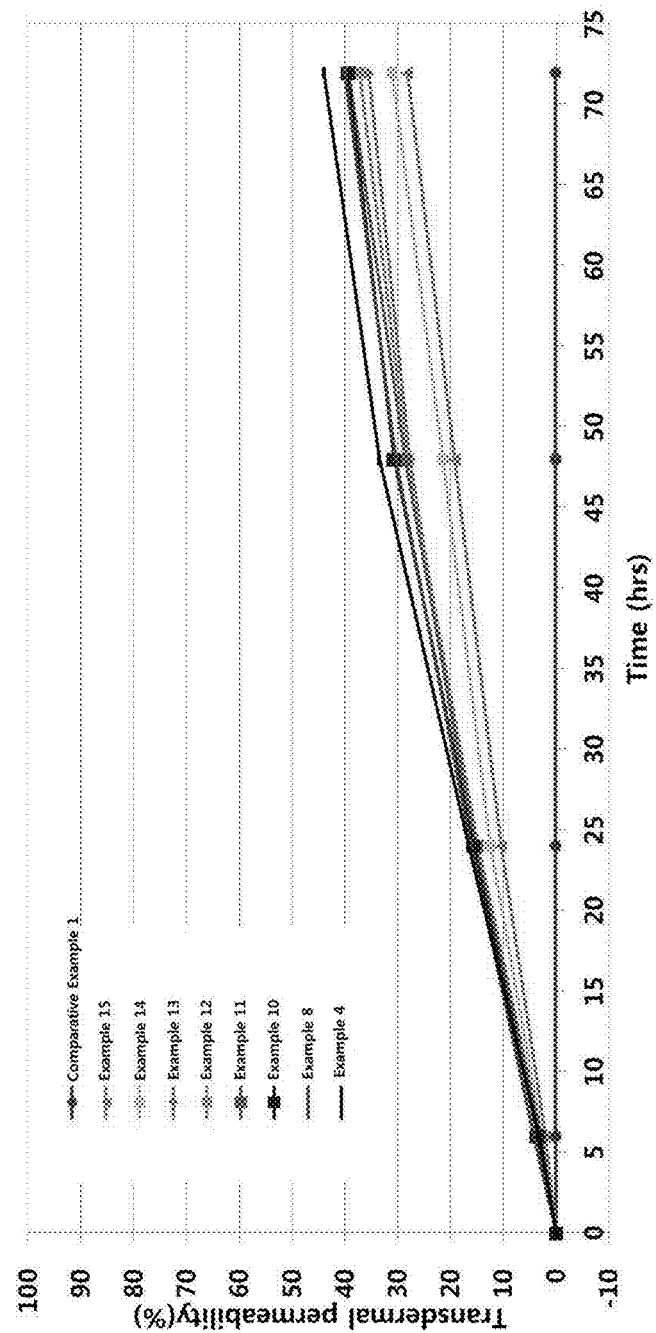

[FIG. 2]
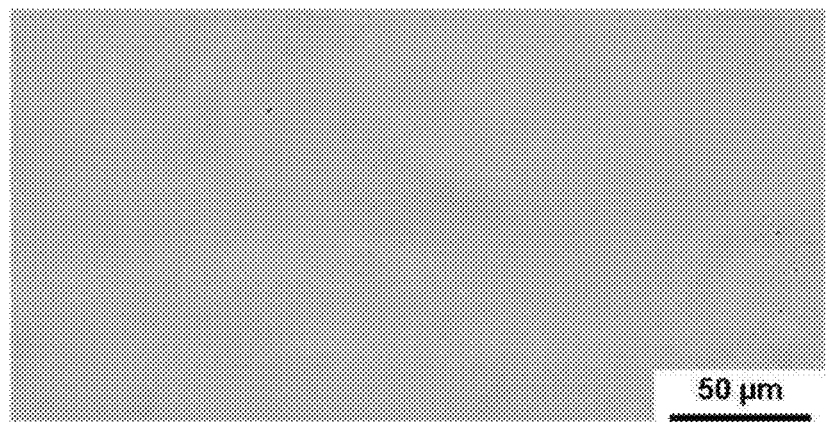

[FIG. 3]
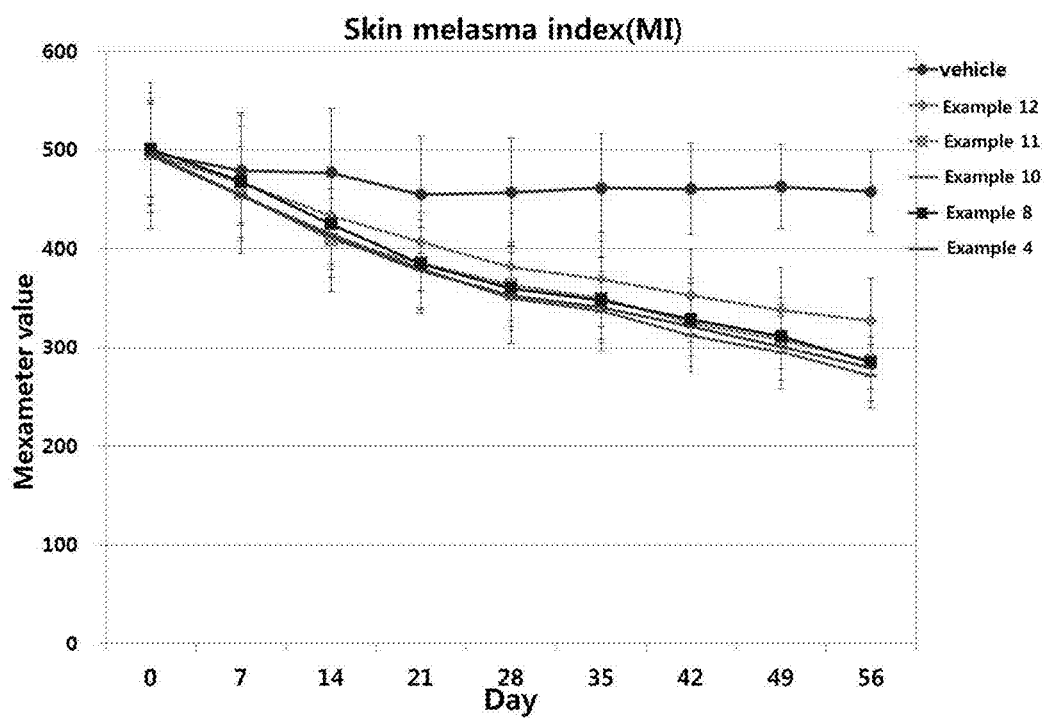

COMPOSITION FOR EXTERNAL USE PREPARATION WITH IMPROVED TRANSDERMAL PERMEABILITY

CROSS-REFERENCE TO RELATED APPLICATION(S)

This is a U.S. national stage entry of International Patent Application No. PCT/KR2014/002676, filed on Mar. 28, 2014, which claims priority to Korean Patent Application No. 10-2014-0036904, filed on Mar. 28, 2014, and Korean Patent Application No. 10-2013-0036912, filed on Apr. 4, 2013, the entire contents of all of which are fully incorporated herein by reference.

TECHNICAL FIELD

The present invention relates to a skin external composition, which includes tranexamic acid or a salt thereof and a transdermal permeation enhancer, thereby showing remarkably increased skin permeability and improved sense of use, skin irritation, and storage stability.

BACKGROUND ART

In general, tranexamic acid functions as a hemostatic agent when orally taken, and also functions as an anticoagulant agent, an anti-allergic agent, or an anti-inflammatory agent when topically applied. Tranexamic acid is used as ethical drugs and is also blended in OTC drugs. Owing to its effects on hyperpigmentation such as melasma, tranexamic acid is used for the treatment of hyperpigmentation and for whitening.

Meanwhile, it has been noted that tranexamic acid has many problems in terms of sense of use, skin irritation, storage stability, and skin permeation, when used as an agent for external use. For example, Korean Patent No. 1087602 indicates a problem that a low-viscosity liquid composition blended with tranexamic acid leaves sticky or thick feeling when applied to the skin, and in particular, the feeling is remarkably increased when more than 0.5% by weight of tranexamic acid is used. Further, Korean Patent No. 1159574 indicates a problem that due to high crystallinity of tranexamic acid, crystals are precipitated in a tranexamic acid-blended agent for external use with evaporation over time. Furthermore, Japanese Patent Publication No. 2010-229100 indicates a problem that tranexamic acid shows very low skin permeability when applied to the skin.

Moreover, the present inventors have analyzed various commercial agents for external use including tranexamic acid as an active ingredient, and as a result, they found that tranexamic acid included in the commercial products does not permeate the human skin in an in-vitro transdermal permeability test (see Experimental Example 1).

DISCLOSURE

Technical Problem

Accordingly, the present inventors have developed a skin external composition which allows skin permeation of tranexamic acid without skin irritation and exhibits excellent sense of use and no precipitation of tranexamic acid in storage, thereby completing the present invention.

Technical Solution

The present invention provides a skin external composition which allows skin permeation of tranexamic acid without skin irritation and exhibits excellent sense of use and storage stability.

To this end, an object of the present invention is to provide a skin external composition including tranexamic acid or a salt thereof and a skin penetration enhancer.

Another object of the present invention is to provide a method for enhancing skin permeability of tranexamic acid or a salt thereof, including the step of applying the composition including tranexamic acid or a salt thereof and a skin penetration enhancer to the skin.

Effect of the Invention

The present invention provides a stable skin external composition which allows high skin permeation of tranexamic acid without skin irritation and exhibits excellent sense of use and no precipitation of tranexamic acid crystals in storage, and therefore, it may be applied to a variety of drugs and cosmetics employing tranexamic acid as an active ingredient.

BRIEF DESCRIPTION OF DRAWINGS

FIG. 1 shows results of measuring transdermal permeability (%) of formulations of Examples 4, 8, and 10~15 and Comparative Example 1 over time.

FIG. 2 shows stability of the formulation of Example 4, which was observed under a microscope.

FIG. 3 shows results of measuring skin melasma index of a negative control group (vehicle) and the formulations of Examples 4, 8, and 10~12.

BEST MODE FOR CARRYING OUT THE INVENTION

In an aspect, the present invention relates to a skin external composition including tranexamic acid or a salt thereof and a skin penetration enhancer.

In another aspect, the present invention relates to a method for enhancing skin permeability of tranexamic acid or a salt thereof, including the step of applying the composition including tranexamic acid or a salt thereof and a skin penetration enhancer to the skin.

In the present invention, tranexamic acid (TA) has a chemical name of 4-(aminomethyl)cyclohexanecarboxylic acid, and is a lysine derivative which acts by reversibly blocking lysine binding sites on plasmin or plasminogen. Therefore, tranexamic acid is an antiplasmin agent, and it has anticoagulant, anti-allergic, and anti-inflammatory effects and inhibitory effects on hyperpigmentation, such as melasma, blemish, freckle, or skin tone or skin texture improvement.

In the present invention, tranexamic acid may be used in the form of a pharmaceutically or cosmetically acceptable salt, and the salt may include salts derived from inorganic acids, organic acids, or bases. For example, an alkali metal salt such as a gallium salt or a magnesium salt, an alkaline earth metal salt, an inorganic acid salt such as sulfate may be used. Further, tranexamic acid or a salt thereof may be synthesized by a method known in the art, or may be purchased from a commercially available source.

In addition to the tranexamic acid of the present invention or a salt thereof, a derivative thereof may be applied, and known derivatives of tranexamic acid may be exemplified by dimers of tranexamic acid [trans-4-(trans-4-aminomethylcyclohexanecarbonyl) aminomethylcyclohexane carboxylate hydrochloride], esters of tranexamic acid and hydroxyquinone (trans-4-aminomethylcyclohexane carboxylate-4'-hydroxyphenylester), esters of tranexamic acid and gentisic acid [2-(trans-4-aminomethylcyclohexylcarbonyloxy)-5-hydroxybenzoic acid and its salts], amides of tranexamic acid [trans-4-aminomethylcyclohexanecarboxylate methylamides and their salts, trans-4-acetylaminomethylcyclohexane carboxylic acids and their salts, trans-4-(p-methoxybenzoyl) aminomethylcyclohexane carboxylic acids and their salts, trans-4-guanidinomethylcyclohexane carboxylic acids and their salts etc.] etc.

In the composition for skin external use of the present invention, tranexamic acid or a salt thereof may be included in an amount of 0.01 to 10% by weight, based on the total weight of the composition. If the amount is less than the above range, it is difficult to expect a noticeable effect. If the amount exceeds the above range, skin permeability may be increased, but solubility of the composition base may be decreased to reduce stability or dispersion of the main ingredient.

In the present invention, tranexamic acid is blended with a skin penetration enhancer, thereby providing a skin external composition showing remarkably enhanced skin absorption of tranexamic acid.

Referring to Experimental Example 1 of the present invention, it can be seen that a commercially available tranexamic acid-containing composition for external use and a tranexamic acid-containing composition for external use disclosed in the prior art show no permeation of tranexamic acid through the human skin, regardless of time.

Therefore, the present invention provides a skin external composition including tranexamic acid, which shows skin permeability of 10% or higher, 15% or higher, or 25% or higher after the composition is applied to the skin for 24 hrs, 48 hrs, or 72 hrs, respectively.

Further, the composition of the present invention may include a skin penetration enhancer in an amount of 1 to 10% by weight, and more preferably, 2 to 5% by weight, based on the total weight of the composition, thereby showing excellent sense of use without skin irritation. If the content is less than the above range, it is difficult to achieve the transdermal absorption rate as intended in the present invention. If the content exceeds the above range, skin irritation may be caused and sense of use may be deteriorated.

The skin penetration enhancer applied in the present invention may be, but is not limited thereto, one or more selected from the group consisting of sorbitol, isopropyl myristate, concentrated glycerin, propylene glycol monolaurate, polysorbate, butylene glycol, diethylene glycol monoethyl ether, glyceryl monooleate, polyglyceryl-6 dioleate, oleoyl polyoxyl-6 glycerides, caprylocaproyl polyoxyl glycerides, linoleoyl polyoxylglycerides, triglycerides, propylene glycol dicaprylocaprate, caprylic capric triglycerides, glycerol caprylate, and polyoxyethylene caprylic/capric glycerides (PEG-6 caprylic/capric glycerides). Preferably, one or more selected from the group consisting of sorbitol, isopropyl myristate, concentrated glycerin, propylene glycol monolaurate, and polysorbate may be used, but is not limited thereto.

Further, the composition for skin external use of the present invention may be blended with a variety of known components, which are blended in a composition applied to the skin or mucous membrane. These components may be exemplified by a moisturizer, a UV absorber, a UV dispersing agent, vitamins, plant extracts, a skin astringent, an anti-inflammatory agent, a whitening agent, a cell stimulator, a vasodilator, a blood circulation stimulating agent, and a skin function enhancer, in addition to various additives such as a surfactant, a pH adjuster, a pigment, a flavoring agent, a preservative, a sterilizer, a thickener, an antioxidant, a metal ion blocker, a refreshing agent, a deodorizer, etc. A known base or carrier may be also used depending on the formulation.

More preferably, the composition for skin external use of the present invention may further include one or more selected from the group consisting of a surfactant, a pH adjusting agent, and a thickener, thereby further improving sense of use and stability and minimizing skin irritation.

If a surfactant is included, it is included in an amount of 1 to 10% by weight, and more preferably, 3 to 6% by weight, based on the total weight of the composition, thereby reducing the surface tension to help mixing of a water phase with an oil phase.

The surfactant may be exemplified by, but is not limited to, anionic surfactants such as higher fatty acid soaps, alkyl sulfate ester salts, polyoxyethylene alkyl ether sulfates, alkyl ether phosphate ester salts, N-acylamino acid salts, and acryl-N-methyl taurine salts; cationic surfactants such as alkyl trimethyl ammonium chloride and dialkyl dimethyl ammonium chloride; amphoteric surfactants such as alkyl dimethyl aminoacetic acid betaine, alkyl amido dimethyl amino acetic acid betaine, and 2-alkyl-N-carboxy-N-hydroxy imidazolinium betaine; and non-ionic surfactants such as polyoxyethylene, polyol ester, and ethylene oxide-propylene oxide block copolymers. Surfactants belonging to polymeric surfactants or natural surfactants may be also used without particular limitation.

If a pH adjusting agent is included, it is included in an amount of 0.01 to 2% by weight, and more preferably, 0.1 to 0.5% by weight, based on the total weight of the composition, thereby maintaining stability of the composition for external use.

The pH adjusting agent may be exemplified by, but is not limited to, sodium hydroxide, boric acid, citric acid, alkanolamide, triethanolamine, acetic acid, sodium hydrogen carbonate, phosphoric acid, ammonia water, sodium sulfite, sodium hexametaphosphate, glucono-delta-lactone, adipic acid, and tetrasodium phosphate.

If a thickener is included, it is included in an amount of 0.01 to 3% by weight, and more preferably, 0.1 to 1.5% by weight, based on the total weight of the composition, thereby providing a proper viscosity.

The thickener may be exemplified by, but is not limited to, hydroxymethyl cellulose, hydroxyethyl cellulose, hydroxypropyl cellulose, carboxyvinyl polymer, alkyl modified carboxyvinyl polymer, polyacrylamide, sodium alginate, propylene glycol alginate, agar, sodium polyacrylate, succinoglucan, dextran, mannan, marmelo, algae colloid, pectin, gellan gum, carrageenan, hyaluronic acid, polyvinyl alcohol, high polymerization degree polyethylene glycol, bentonite, magnesium aluminum silicate, Laponite, hectorite, and silicic anhydride. The metal ion blocker may be exemplified by, but is not limited to, a sodium salt of ethylene diamine tetra-acetic acid, phosphoric acid, and citric acid.

The preservative may be exemplified by ethyl para-hydroxybenzoate, salicylic acid, and sorbic acid.

If the formulation is a paste, a cream, or a gel, a carrier component may be animal oil, vegetable oil, wax, paraffin, starch, tracant, a cellulose derivative, polyethylene glycol, silicon, bentonite, silica, talc, or zinc oxide.

If the formulation is a powder or a spray, a carrier component may be lactose, talc, silica, aluminum hydroxide, calcium silicate, or polyamide powder, and in particular, in the case of spray, a propellent agent, such as chlorofluorohydrocarbon, propane/butane, or dimethyl ether, may be additionally included.

If the formulation is a solution or an emulsion, a carrier component may be a solvent, a solubilizing agent, or an emulsifying agent, and it may be exemplified by water, ethanol, isopropanol, ethyl carbonate, ethyl acetate, benzyl alcohol, benzyl benzoate, propylene glycol, 1,3-butylglycol oil, glycerol aliphatic ester, polyethylene glycol, or fatty acid ester of sorbitan.

If the formulation is a suspension, a carrier component may be a liquid diluent, such as water, ethanol, or propylene; a suspension, such as ethoxylated isostearyl alcohol, polyoxyethylene sorbitol ester, or polyoxyethylene sorbitan ester; microcrystalline cellulose, aluminium metahydroxide, bentonite, agar, or tracant.

The composition for skin external use of the present invention may be directly applied or sprayed onto the skin depending on its type. The amount and frequency of use of the composition per day may be properly determined according to a user's age, gender, use, and degree of symptoms, and for example, a proper amount of the composition may be applied to the skin at a frequency of once a day to 5 or 6 times a day.

The composition for skin external use of the present invention may be applied to a variety of pharmaceutical compositions or cosmetic compositions employing tranexamic acid or a salt thereof as an active ingredient. If the composition may be used as a pharmaceutical composition, it may be used as an anti-plasmin agent, an anticoagulant agent, an anti-allergic agent, an anti-inflammatory agent, or a therapeutic agent for hyperpigmentation. If the composition may be used as a cosmetic composition, it may be used as a functional cosmetic composition for improving melasma, blemish, freckle, skin tone, or skin texture and for whitening the skin.

In a preferred embodiment, the present invention relates to a pharmaceutical composition for external use, including tranexamic acid or a salt thereof and a skin penetration enhancer.

Herein, a medical composition for external use includes a drug and a quasi-drug for external use. The formulation of the medical composition for external use is not particularly limited, as long as it can be applied to the skin or mucous membrane. For example, it may be any formulation such as an aqueous solution system, a soluble system, an emulsion system, a powder dispersion system, and a water/oil two layer system. Specifically, a liquid, an emulsion, a lotion, a liniment, an emulsion, a suspension, a cream, or an ointment may be exemplified.

When the composition may be used for treating and improving hyperpigmentation, a known whitening component may be further blended, and exemplified by pantothenic acid or a salt thereof, hydroquinones, glucosamines, hinokitiols, azelaic acid or a salt thereof, tocopherols, pyridoxine or a salt thereof, ubiquinones, carotenes, flavones, iso flavones, flavanones, catechins, flavonols, glycinates, kojic acid or a salt thereof, glutathione or a salt thereof, other natural extracts having a whitening activity, but is not limited thereto.

In another preferred embodiment, the present invention relates to a cosmetic composition including tranexamic acid or a salt thereof and a skin penetration enhancer. The cosmetic composition according to the present invention is characterized in that it includes tranexamic acid or a salt thereof as an active ingredient, thereby showing the effects of improving and whitening melasma, blemish, freckle, skin tone, skin texture, and inflammatory hyperpigmentation.

The cosmetic composition according to the present invention may include tranexamic acid or a salt thereof in an amount of 0.01 to 10% by weight, based on the total weight of the composition. If the amount is less than the above range, it is difficult to expect a noticeable effect. If the amount exceeds the above range, skin permeability may be increased, but solubility of the composition base may be decreased to reduce stability or dispersion of the main ingredient.

The composition according to the present invention may be formulated into a cosmetic composition in an embodiment of the present invention, which may be exemplified by cosmetics. In this case, the cosmetic composition according to the present invention includes a cosmetically or dermatologically acceptable medium or base. Such composition includes any formulations suitable for local applications, for example, a solution, a gel, a solid, anhydrous paste products, oil in water emulsion, a suspension, a microemulsion, microcapsules, microgranules or ionic (liposome) and non-ionic vesicular dispersion, or may be provided in the form of a cream, a skin, a lotion, a powder, an ointment, a spray, or a conceal stick. Such compositions may be obtained in a manner generally known in the art. Further, the composition according to the present invention may be used in the form of a foam or an aerosol composition further including a pressurized propellant.

Further, the cosmetic composition according to the present invention may include an adjuvant currently used in the field of cosmetics and dermatology, such as fat, an organic solvent, a dissolving agent, a concentrating agent, a gelling agent, a softener, an anti-oxidant, a suspending agent, a stabilizer, a foaming agent, a fragrance, a surfactant, water, an ionic or non-ionic emulsifier, a filler, a metal ion blocker, a chelating agent, a preservative, vitamins, a blocking agent, a wetting agent, essential oil, a dye, a pigment, a hydrophilic or hydrophobic activating agent, lipid vesicles or other ingredients currently used in cosmetic products. Such adjuvant may be used in an amount currently used in the field of cosmetics or dermatology.

The cosmetic composition according to the present invention may be properly prepared in any desired formulation with no particular limitation. For example, the cosmetic composition may be prepared into a formulation such as a skin softener (skin lotion and milk lotion), a nutrient tonic, an essence, a nutrient cream, a massage cream, an eye cream, an eye essence, a pack, a patch, a gel, a stick, a spray, a cleansing cream, a cleansing foam, a cleansing water, a pack, a powder, a body lotion, a body cream, a body oil, or a body essence, but is not limited thereto.

In an embodiment of the present invention, the composition may be applied to the face, in particular, eyes, mouth, cheeks, forehead, neck, hands or feet, but is not limited thereto.

DETAILED DESCRIPTION OF THE EMBODIMENTS

Hereinafter, the present invention will be described in detail with reference to Examples. However, these Examples are for illustrative purposes only, and the present invention is not limited to the following Examples.

Comparative Example 1. White Lucent (Shiseido)

White Lucent (Shiseido, Japan) was purchased and prepared. The main raw materials of White Lucent are summarized in Table 1.

TABLE 1

| Name of raw material |
| --- |
| 2-0-Ethyl ascorbic acid |
| Glucosyl hesperidin |
| Glycerin |
| Dimethicone |
| Disodium EDTA |
| Lauly betaine |
| Limonene |
| Benzyl benzoate |
| Butylene glycol |
| Serine |
| Cetyl ethyl hexanoate |
| Sodium metabisulfite |
| Sodium benzoate |
| Sodium hyaluronate |
| Aminomethyl propanediol |
| Acrylate/C10-30 alkyl acrylate copolymer |
| Isostearic acid |
| Xanthan gum |
| Purified water |
| Carbomer |
| Tocopherol acetate |
| Tranexamic acid |
| Phenoxyethanol |
| Potassium methoxysalicylate |
| Polyquaternium-51 |
| PEG/PPG-14/dimethyl ester |
| PEG-150 |
| Fragrance (natural) |

Comparative Example 2. Aestura RegeDerm Rx (Amore Pacific)

Aestura RegeDerm Rx (Amore Pacific, Korea) was purchased and prepared. The main raw materials of Aestura RegeDerm Rx are summarized in Table 2.

TABLE 2

| Name of raw material |
| --- |
| Tranexamic acid |
| Glycolic acid |
| Glycerin |
| Glyceryl stearate |
| Glyceryl caprylate |
| Niacinamide |
| Disodium EDTA |
| Beta-glucan |
| Butylene glycol |
| Cyclopentasiloxane |
| Cyclohexasiloxane |
| Salicylic acid |
| Cetyl alcohol |
| Ceteth-20 |
| Cetearyl alcohol |
| Sodium lactate |
| Sodium polyacrylate |
| Sodium hyaluronate |
| Steareth-20 |
| Stearic acid |
| Ethanol |
| Ethoxydiglycol |
| Inulin lauryl carbamate |

TABLE 2-continued

| Name of raw material |
| --- |
| Tocophersolan |
| Tromethamine |
| Phenoxyethanol |
| Poloxamer 235 |
| Poloxamer 338 |
| Polyglyceryl-3 methylglucose distearate |
| Propanediol |
| PEG-75 stearate |
| Hydrogenated lecithin |
| Hydrogenatedpoly |
| Fragrance (natural) |
| Hexapeptide-9 Epigallocatechin gallate |

Comparative Example 3. Cream Formulation of Example 52 of Korean Patent No. 10-0251813

A cream formulation of Example 52 of Korean Patent No. 10-0251813 was prepared. The main raw materials and content thereof are summarized in Table 3.

TABLE 3

| Name of raw material | Content (% by weight) |
| --- | --- |
| Tranexamic acid | 2.00 |
| Stearyl alcohol | 1.50 |
| Squalene | 2.00 |
| Vaseline | 2.50 |
| Deodorized liquid lanolin | 1.50 |
| Evening primrose oil | 2.00 |
| Isopropyl myristate | 5.00 |
| Glycerin monooleate | 2.00 |
| Polyoxyethylene (60 mol) hydrogenated castor oil | 2.00 |
| Tocopherol acetate | 0.05 |
| Ethyl parahydroxybenzoate | 0.20 |
| Butyl parahydroxybenzoate | 1.00 |
| Trans-4-ureidomethylcyclohexanecarboxylic acid | 1.00 |
| Trans-4-(N'-ethylureidomethyl)cyclohexanecarboxylic acid | 1.00 |
| Fragrance | q.s. |
| Sodium hydrogensulfite | 0.01 |
| Glycerin | 5.00 |
| Sodium hyaluronate | 0.01 |
| Carboxyl vinyl polymer | 0.20 |
| Potassium hydroxide | 0.20 |
| Purified water | balance |

Examples 1-15

Formulations Containing Tranexamic Acid and Transdermal Absorber

Formulations of Examples 1 to 10 were prepared according to the compositions given in the following Table 4, and Formulations of Examples 11 to 15 were prepared according to the compositions given in the following Table 5.

TABLE 4

| Name of raw material | Example 1 | Example 2 | Example 3 | Example 4 | Example 5 | Example 6 | Example 7 | Example 8 | Example 9 | Example 10 |
|---|---|---|---|---|---|---|---|---|---|---|
| | | | | | Content (% by weight) | | | | | |
| Tranexamic acid | 10.00 | 10.00 | 10.00 | 10.00 | 10.00 | 10.00 | 5.00 | 5.00 | 2.00 | 2.00 |
| Sorbitol | 2.50 | — | — | 5.00 | — | — | — | — | — | — |
| Isopropyl myristate | — | 2.50 | — | — | 5.00 | — | — | — | — | — |
| Concentrated glycerin | — | — | 2.50 | — | — | 5.00 | 2.50 | — | — | — |
| Propylene glycol monolaurate | — | — | — | — | — | — | — | 5.00 | 2.50 | — |
| Polysorbate | — | — | — | — | — | — | — | — | — | 5.00 |
| Glycol stearate | 2.90 | 2.90 | 2.90 | 2.90 | 2.90 | 2.90 | 2.90 | 2.90 | 2.90 | 2.90 |
| diethylene glycol monoethyl ether | 5.00 | 5.00 | 5.00 | 5.00 | 5.00 | 5.00 | 5.00 | 5.00 | 5.00 | 5.00 |
| Butylated hydroxy toluene | 0.10 | 0.10 | 0.10 | 0.10 | 0.10 | 0.10 | 0.10 | 0.10 | 0.10 | 0.10 |
| Cetyl alcohol | 1.00 | 1.00 | 1.00 | 1.00 | 1.00 | 1.00 | 1.00 | 1.00 | 1.00 | 1.00 |
| Olive oil | 1.00 | 1.00 | 1.00 | 1.00 | 1.00 | 1.00 | 1.00 | 1.00 | 1.00 | 1.00 |
| Liquid paraffin | 2.00 | 2.00 | 2.00 | 2.00 | 2.00 | 2.00 | 2.00 | 2.00 | 2.00 | 2.00 |
| Purified water | 75.15 | 75.15 | 75.15 | 72.65 | 72.65 | 72.65 | 80.15 | 77.65 | 83.15 | 80.65 |
| Carbomer 940 | 0.10 | 0.10 | 0.10 | 0.10 | 0.10 | 0.10 | 0.10 | 0.10 | 0.10 | 0.10 |
| Tocopherol acetate | 0.05 | 0.05 | 0.05 | 0.05 | 0.05 | 0.05 | 0.05 | 0.05 | 0.05 | 0.05 |
| Triethanolamine | 0.10 | 0.10 | 0.10 | 0.10 | 0.10 | 0.10 | 0.10 | 0.10 | 0.10 | 0.10 |
| Fragrance | 0.10 | 0.10 | 0.10 | 0.10 | 0.10 | 0.10 | 0.10 | 0.10 | 0.10 | 0.10 |

TABLE 5

| Name of raw material | Example 11 | Example 12 | Example 13 | Example 14 | Example 15 |
|---|---|---|---|---|---|
| | | | Weight (%) | | |
| Tranexamic acid | 1.00 | 0.50 | 0.30 | 0.10 | 0.05 |
| Sorbitol | 5.00 | 5.00 | 5.00 | 5.00 | 5.00 |
| Isopropyl myristate | — | — | — | — | — |
| Concentrated glycerin | — | — | — | — | — |
| Propylene glycol monolaurate | — | — | — | — | — |
| Polysorbate | — | — | — | — | — |
| Glycol stearate | 2.90 | 2.90 | 2.90 | 2.90 | 2.90 |
| diethylene glycol monoethyl ether | 5.00 | 5.00 | 5.00 | 5.00 | 5.00 |
| Butylated hydroxy toluene | 0.10 | 0.10 | 0.10 | 0.10 | 0.10 |
| Cetyl alcohol | 1.00 | 1.00 | 1.00 | 1.00 | 1.00 |
| Olive oil | 1.00 | 1.00 | 1.00 | 1.00 | 1.00 |
| Liquid paraffin | 2.00 | 2.00 | 2.00 | 2.00 | 2.00 |
| Purified water | 81.65 | 82.15 | 82.35 | 82.55 | 82.60 |
| Carbomer 940 | 0.10 | 0.10 | 0.10 | 0.10 | 0.10 |
| Tocopherol acetate | 0.05 | 0.05 | 0.05 | 0.05 | 0.05 |
| Triethanolamine | 0.10 | 0.10 | 0.10 | 0.10 | 0.10 |
| Fragrance | 0.10 | 0.10 | 0.10 | 0.10 | 0.10 |

Preparation methods of the formulations of Examples 1 to 15 are summarized in the following Table 6.

TABLE 6

| Process | Operation |
|---|---|
| Preparation of aqueous phase | Purified water was added to a preparation tank and then tranexamic acid was agitated at room temperature for 10 minutes. When tranexamic acid was completely dissolved, carbomer 940 was slowly added and completely dissolved. Temperature: room temperature Agitation speed: homomixer: 3,000 rpm |
| Preparation of oil phase | An assistant preparation tank was heated, and then liquid paraffin, sorbitol (or isopropyl myristate, propylene glycol monolaurate, polysorbate, concentrated glycerin), olive oil, cetyl alcohol, glycol stearate, and butylated hydroxytoluene were sequentially added and completely dissolved. Temperature: 65~75° C. Agitation speed: homomixer: 3,000 rpm |
| Emulsification | While agitating the preparation tank, the oil phase liquid was slowly added to the aqueous phase liquid of the preparation tank, and then tocopherol acetate and diethylene glycol monoethyl ether were added and agitated with heating. Temperature: 60~70° C. Agitation speed: homomixer: 3,000 rpm |

TABLE 6-continued

| Process | Operation |
|---|---|
| Cooling | While cooling the tank, triethanolamine and fragrance were added and agitated, and then bubbles were removed under reduced pressure. Temperature: 40° C. Agitation speed: homomixer: 3,000 rpm Reduced pressure: 70 mmHg |
| Filtration | Filtration was performed using a 80 mesh, and then the product was transferred to a semi-finished container. |

Experimental Example 1. Transdermal Permeability Test 1-1. Conditions for Transdermal Permeability Test
Receptor: PBS (0.1% sodium azide)
Skin area contacting with receptor phase: 0.636 $cm^2$
Volume of receptor phase: 4.7 ml
Skin: a man aged 50 years
Temperature: 32° C.
Agitation speed: 600 rpm
Amount of sample collected: 1 ml per hr
1-2. Test Method
Skin permeation of tranexamic acid from the composition for external use through the human cadaver skin was measured using Franz diffusion cells. Franz diffusion cells were filled with receptors and agitated at 600 rpm while maintaining the temperature at 32° C.

The human cadaver skin was placed between donor and receptor compartments of the Franz diffusion cells. The test drug was measured and loaded on the skin. As test solutions, 1 ml of receptor phase was collected at 6, 24, 48 and 72 hrs from a sampling port using a syringe, and quantification was performed by HPLC. The receptor at 32° C. was immediately added at an amount equal to the amount collected.
1-3. Analysis Method
The contents of tranexamic acid in the standard solution and the test solution were analyzed by the following liquid chromatography, and then a peak area was determined to prepare a calibration curve of the standard solution, and skin permeability was calculated therefrom.
1-4. Test Equipment
Equipment: HPLC
Model: Agilent 1100 Series
1-5. Analysis Conditions
<Conditions for Liquid Chromatography>
Column: Capcell pak (150 mm×4.6 mm, 5 μm)
Column temperature: 30° C.
Flow rate: 1 ml/min
Detection: UV 220 nm
Injection amount: 100 μl Mobile phase: 11.0 g of anhydrous sodium dihydrogen phosphate was dissolved in 500 ml of water, and 5 ml of triethylamine and 1.4 g of sodium lauryl sulfate were added thereto. pH was adjusted to 4.0 with phosphate, and water was added to bring the volume to 600 ml. 400 ml of methanol was added to this solution.
<Preparation of Standard Solution>
Tranexamic acid standard solution: 10 mg of tranexamic acid was dissolved in a receptor solution, and then diluted with the receptor solution to prepare a standard solution (5, 20, 35, 50, 65 μg/ml).
1-6. Equation
C (concentration, μg/ml)=(peak area of test solution−intercept of calibration curve)/slope of calibration curve
Cumulative permeability (Amount, $\mu g/cm^2$)=((Cn×4.7)+ (C1+C2+ . . . +Cn)×1)/0.636
n=time point of collection of test solution
Transdermal permeation rate (Flux, $\mu g/cm^2/hr$)=((Cn× 4.7)+(C1+C2+ . . . +Cn)×1)/0.636/T n=time point of collection of test solution, T=time of collection of test solution
1-7. Test Result
Transdermal permeabilities (%) of the formulations of Examples 4, 8, and 10-15, and the formulations of Comparative Examples 1, 2, and 3 were measured over time and summarized in the following Tables 7 and 8 and FIG. 1. The formulations of Comparative Examples 1, 2, and 3 showed no transdermal permeation, regardless of time, whereas the formulations of Examples showed high transdermal permeability and their transdermal permeabilities continuously increased over time.

TABLE 7

| | Average permeability (%) | | |
|---|---|---|---|
| Time (h) | Comparative Example 1 | Comparative Example 2 | Comparative Example 3 |
| 0 | 0.00 | 0.00 | 0.00 |
| 6 | 0.00 | 0.00 | 0.00 |
| 24 | 0.00 | 0.00 | 0.00 |
| 48 | 0.00 | 0.00 | 0.00 |
| 72 | 0.00 | 0.00 | 0.00 |

TABLE 8

| | Average permeability (%) | | | | | | | |
|---|---|---|---|---|---|---|---|---|
| Time (h) | Example 4 | Example 8 | Example 10 | Example 11 | Example 12 | Example 13 | Example 14 | Example 15 |
| 0 | 0.00 | 0.00 | 0.00 | 0.00 | 0.00 | 0.00 | 0.00 | 0.00 |
| 6 | 3.31 | 4.22 | 3.58 | 3.01 | 2.84 | 3.09 | 2.69 | 2.12 |
| 24 | 16.66 | 16.22 | 15.65 | 15.22 | 14.87 | 16.00 | 12.54 | 10.50 |
| 48 | 33.54 | 30.38 | 30.74 | 28.64 | 28.17 | 27.82 | 21.38 | 19.18 |
| 72 | 44.04 | 40.07 | 39.46 | 39.34 | 37.36 | 35.59 | 31.08 | 28.24 |

Experimental Example 2. Skin Irritation Test

In accordance with the guidelines for drug toxicity test, a skin irritation test was performed by applying the test material to the skin, and then 24 hrs later, briefly washing the skin with a solvent such as physiological saline which does not influence the test result in order to completely remove the test material, and observing changes such as erythema, edema, bleeding, and eschar formation after 24, 48, and 72 hrs.

Eschar formation was evaluated in accordance with the criteria of the following Table 9, and edema was evaluated in accordance with the criteria of the following Table 10.

TABLE 9

| Grading scale | |
| --- | --- |
| No erythema | 0 |
| Very slight erythema (barely perceptible) | 1 |
| Well-defined erythema | 2 |
| Moderate to severe erythema | 3 |
| Severe erythema (beet redness) and slight eschar formation | 4 |
| Possible total erythema score | 4 |

TABLE 10

| Grading scale | |
| --- | --- |
| No edema | 0 |
| Very slight edema (barely perceptible) | 1 |
| Slight edema (edges of area well defined by definite raising) | 2 |
| Moderate edema (raised approximately 1 mm) | 3 |
| Severe edema (raised more than 1 mm and extending beyond the area of exposure) | 4 |
| Possible total edema score | 4 |

In accordance with the above criteria, skin irritation of the formulations of Examples 4, 8, and 10-15 and the formulations of Comparative Examples 1, 2, and 3 was tested, and the results are summarized in the following Table 11. All the formulations showed no skin irritation.

TABLE 11

| Section | Degree of skin irritation |
| --- | --- |
| Example 4 | 0 |
| Example 8 | 0 |
| Example 10 | 0 |
| Example 11 | 0 |
| Example 12 | 0 |
| Example 13 | 0 |
| Example 14 | 0 |
| Example 15 | 0 |
| Comparative Example 1 | 0 |
| Comparative Example 2 | 0 |
| Comparative Example 3 | 0 |

Experimental Example 3. Test of Sense of Use

To test sense of use, the test material was applied, and 10 minutes later, changes in three items of stickiness, glossiness, and thickness were examined Evaluation criteria are summarized in Table 12.

TABLE 12

| Evaluation criteria for sense of use | | | | |
| --- | --- | --- | --- | --- |
| ☆ | ◎ | ○ | Δ | X |
| Very good | Good | Moderate | Slightly bad | Bad |

The results of evaluating the sense of use of the formulations of Examples 4, 8, and 10-15 and the formulations of Comparative Examples 1, 2, and 3 in accordance with the above criteria are summarized in the following Table 13.

TABLE 13

| Section | Stickiness | Glossiness | Thickness |
| --- | --- | --- | --- |
| Comparative Example 1 | ☆ | ◎ | ◎ |
| Comparative Example 2 | ◎ | ○ | ◎ |
| Comparative Example 3 | ◎ | ◎ | ◎ |
| Example 4 | ○ | ☆ | ○ |
| Example 8 | ○ | ☆ | ○ |
| Example 10 | ◎ | ◎ | ◎ |
| Example 11 | ◎ | ◎ | ◎ |
| Example 12 | ◎ | ◎ | ☆ |
| Example 13 | ☆ | ○ | ☆ |
| Example 14 | ☆ | ○ | ☆ |
| Example 15 | ☆ | ○ | ☆ |

Experimental Example 4. Stability Test (Accelerated Test)

In accordance with the guidelines for drug stability test, the test was performed at 40±2° C./relative humidity 75±5%. According to the above evaluation criteria, stability of the formulations of Examples 4, 6, and 8 was tested. As a result, as shown in FIG. 2, no crystal precipitation was observed under a microscope.

As shown in the following Table 14, the formulations of Examples 4, 8, and 10~15 showed stability in both content and appearance.

TABLE 14

Stability test results of formulations of Examples 4, 8, and 10~15
Accelerated stability test (storage conditions: 40 ± 2° C., 75 ± 5% RH)

| Section | Test item | Criteria | Test results | | | |
| --- | --- | --- | --- | --- | --- | --- |
| | | | Initial | 2 months | 4 months | 6 months |
| Example 4 | Appearance | White cream formulation | Suitable | Suitable | Suitable | Suitable |
| | Content | 90.0~110.0% | 100.89 | 100.62 | 100.37 | 100.05 |
| Example 8 | Appearance | White cream formulation | Suitable | Suitable | Suitable | Suitable |
| | Content | 90.0~110.0% | 101.03 | 100.55 | 100.63 | 100.29 |
| Example 10 | Appearance | White cream formulation | Suitable | Suitable | Suitable | Suitable |
| | Content | 90.0~110.0% | 100.39 | 100.89 | 99.72 | 99.84 |
| Example 11 | Appearance | White cream formulation | Suitable | Suitable | Suitable | Suitable |
| | Content | 90.0~110.0% | 100.22 | 100.51 | 100.33 | 99.91 |

TABLE 14-continued

Stability test results of formulations of Examples 4, 8, and 10~15
Accelerated stability test (storage conditions: 40 ± 2° C., 75 ± 5% RH)

| Section | Test item | Criteria | Initial | 2 months | 4 months | 6 months |
|---|---|---|---|---|---|---|
| Example 12 | Appearance | White cream formulation | Suitable | Suitable | Suitable | Suitable |
| | Content | 90.0~110.0% | 100.75 | 100.83 | 100.79 | 99.81 |
| Example 13 | Appearance | White cream formulation | Suitable | Suitable | Suitable | Suitable |
| | Content | 90.0~110.0% | 100.11 | 99.87 | 100.07 | 100.18 |
| Example 14 | Appearance | White cream formulation | Suitable | Suitable | Suitable | Suitable |
| | Content | 90.0~110.0% | 100.27 | 100.29 | 100.03 | 100.07 |
| Example 15 | Appearance | White cream formulation | Suitable | Suitable | Suitable | Suitable |
| | Content | 90.0~110.0% | 100.57 | 100.27 | 100.07 | 100.08 |

Experimental Example 5. Efficacy Test 5-1. Experimental Animal
Species: Brown Guinea Pig (Al)
Sex and weight: male, 500~550 g
Breeding environment:
Temperature 23±3° C.,
Relative humidity 50±10%,
Lighting 12 hr (08:00~20:00),
Number of air circulation 10~15 times/hr,
Illumination 150~300 Lux.

5-2. Pretreatment (UV Tanning)
Experimental animals were brought and acclimated, and the hair of the animal's back was shaved. The animals were anesthetized with Zoletil, and the shaved area was covered with a perforated leather, followed by UV irradiation once a week for 3 weeks (500 mJ/cm$^2$*3 times=1,500 mJ/cm$^2$) for induction of melanin pigmentation. A mexameter was used to measure pigmentation (melasma index).

5-3. Treatment of Test Material
Each 30 μl of the test materials (vehicle, Examples 4, 8, and 10-12) was applied to the induced pigment spot once a day for 5 days a week for 8 weeks. After treatment of the test material, a mexameter was used to measure skin melasma index once a week (measurement of the index for the same area was repeated three times, and the mean value was used).

5-4. Test Results
The test results of melasma index are shown in Table 15 and FIG. 3.

TABLE 15

| Time | vehicle | | Example 4 | | Example 8 | | Example 10 | | Example 11 | | Example 12 | |
|---|---|---|---|---|---|---|---|---|---|---|---|---|
| (day) | Mean | SD | Mean | SD | Mean | SD | Mean | SD | Mean | SD | Mean | SD |
| 0 | 497.2 | 60.5 | 496.6 | 44.6 | 500.7 | 48.8 | 494.0 | 73.6 | 495.6 | 50.5 | 495.7 | 51.8 |
| 7 | 479.1 | 55.6 | 454.2 | 55.2 | 468.0 | 56.1 | 453.8 | 27.6 | 455.6 | 47.7 | 466.4 | 71.2 |
| 14 | 476.8 | 65.3 | 411.9 | 50.3 | 425.1 | 54.3 | 414.6 | 35.9 | 408.9 | 51.8 | 433.7 | 49.0 |
| 21 | 454.9 | 59.3 | 377.6 | 42.9 | 384.8 | 44.5 | 380.1 | 41.8 | 385.9 | 50.9 | 406.9 | 49.7 |
| 28 | 457.1 | 54.7 | 353.0 | 37.7 | 360.1 | 42.8 | 350.0 | 45.9 | 363.8 | 42.8 | 381.7 | 53.9 |
| 35 | 461.6 | 54.5 | 340.4 | 39.4 | 348.0 | 43.0 | 336.9 | 40.7 | 349.8 | 41.6 | 369.1 | 47.7 |
| 42 | 460.7 | 46.1 | 321.2 | 37.6 | 328.6 | 36.9 | 312.7 | 37.6 | 325.4 | 44.7 | 352.7 | 46.8 |
| 49 | 462.8 | 42.4 | 300.7 | 43.1 | 311.3 | 32.7 | 294.9 | 36.9 | 308.3 | 41.7 | 337.8 | 43.1 |
| 56 | 457.9 | 40.4 | 279.1 | 34.7 | 284.3 | 26.2 | 271.1 | 32.3 | 286.2 | 40.1 | 327.2 | 42.8 |

The invention claimed is:

1. A method for enhancing skin permeability of tranexamic acid or a salt thereof, comprising the step of applying a skin external composition in the form of a soluble system or an emulsion system consisting of:
   (i) tranexamic acid or a salt thereof, and
   (ii) a skin penetration enhancer, which is a combination of
      (a) a material selected from the group consisting of sorbitol, isopropyl myristate, and propylene glycol monolaurate, and (b) diethylene glycol monoethyl ether,
   (iii) additives,
   (iv) a surfactant in an amount of 1 to 10% by weight,
   (v) a thickener in an amount of 0.01 to 3% by weight,
   (vi) a pH adjusting agent in an amount of 0.01 to 2% by weight, and
   wherein the skin permeability of tranexamic acid or a salt thereof is 10% to 100% after the composition is applied to a skin for 24 hours.

2. The method of claim 1, wherein the composition comprises tranexamic acid or the salt thereof in an amount of 0.01 to 10% by weight.

3. The method of claim 1, wherein the composition comprises the skin penetration enhancer in an amount of 1 to 10% by weight.

4. The method of claim 1, wherein the surfactant is an anionic surfactant, a cationic surfactant, or an amphoteric surfactant.

5. The method of claim 1, wherein the thickener is selected from the group consisting of hydroxymethyl cellulose, hydroxyethyl cellulose, hydroxypropyl cellulose, carboxyvinyl polymer, alkyl modified carboxyvinyl polymer, polyacrylamide, sodium alginate, propylene glycol alginate, agar, sodium polyacrylate, succinoglucan, dextran, mannan, marmelo, algae colloid, pectin, gellan gum, carrageenan, hyaluronic acid, polyvinyl alcohol, high polymerization degree polyethylene glycol, bentonite, magnesium aluminum silicate, Laponite, hectorite, and silicic anhydride.

6. The method of claim 1, wherein the pH adjusting agent is selected from the group consisting of sodium hydroxide, boric acid, citric acid, alkanolamide, triethanolamine, acetic acid, sodium hydrogen carbonate, phosphoric acid, ammonia water, sodium sulfite, sodium hexametaphosphate, glucono-delta-lactone, adipic acid, and tetrasodium phosphate.

7. The method of claim 1, wherein skin permeability of tranexamic acid or a salt thereof is 15% to 100% after the composition is applied to a skin for 48 hours.

8. The method of claim 1, wherein the composition is a cosmetic composition.

9. The method of claim 1, wherein the composition is a pharmaceutical composition having antiplasmin activity, anticoagulant activity, anti-allergic activity or hyperpigmentation treatment activity.

10. The method of claim 1, wherein the composition has improved storage stability.

* * * * *